Figure 1:
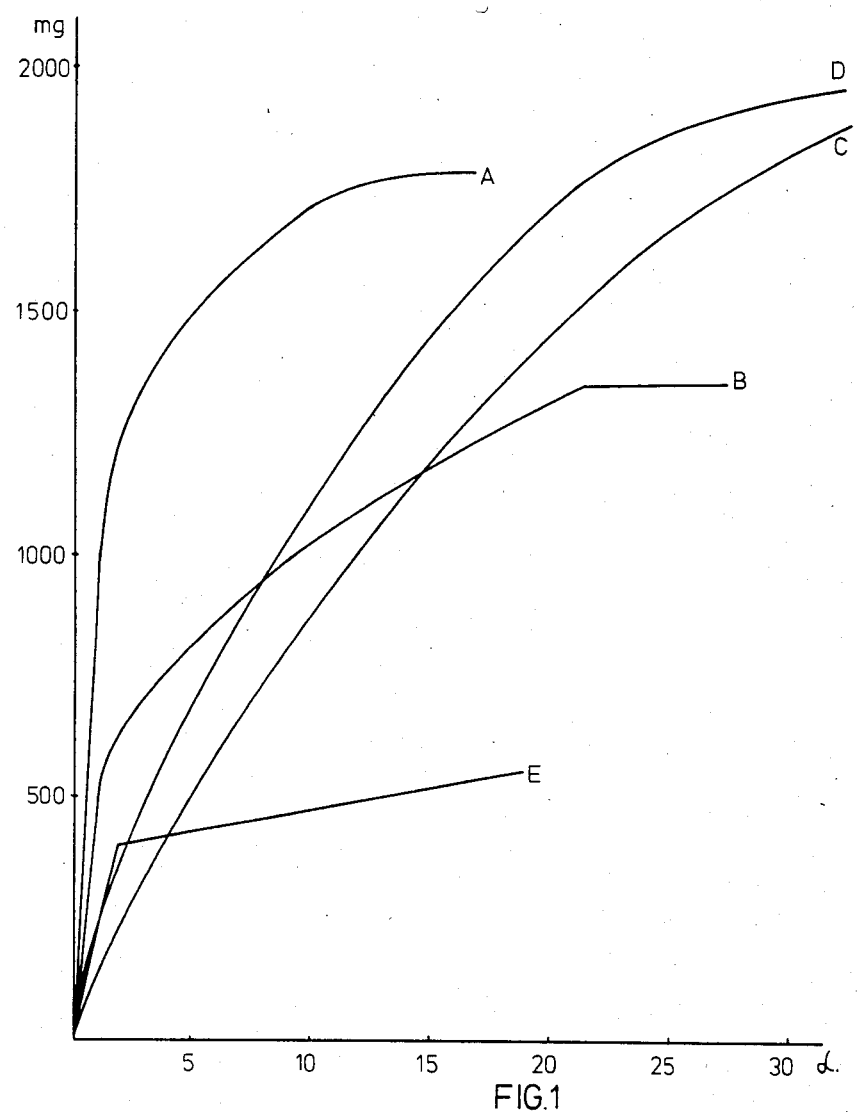

United States Patent [19]

von Bittera et al.

[11] Patent Number: 4,543,247
[45] Date of Patent: Sep. 24, 1985

[54] ECTOPARASITICIDE-CONTAINING COLLARS FOR PETS

[75] Inventors: Miklos von Bittera, Leverkusen; Manfred Federmann, Wuppertal; Ulrich von Gizycki, Leverkusen; Dietmar Schäpel, Cologne; Wilhelm Stendel, Wuppertal; Herbert Voege, Leverkusen; Hubert Dorn, Wuppertal, all of Fed. Rep. of Germany

[73] Assignee: Bayer Aktiengesellschaft, Leverkusen, Fed. Rep. of Germany

[21] Appl. No.: 456,141

[22] Filed: Jan. 6, 1983

Related U.S. Application Data

[63] Continuation of Ser. No. 308,718, Oct. 5, 1981, abandoned.

[30] Foreign Application Priority Data

Oct. 22, 1980 [DE]  Fed. Rep. of Germany ....... 3039881

[51] Int. Cl.$^4$ .................... A01N 25/00; A01N 25/34
[52] U.S. Cl. ........................ 424/14; 424/16; 424/27; 424/78; 119/156
[58] Field of Search ....................... 424/14, 16, 27, 78; 119/156

[56] References Cited

U.S. PATENT DOCUMENTS

| | | | |
|---|---|---|---|
| 3,269,900 | 8/1966 | Rubin | 424/19 |
| 3,708,435 | 1/1973 | Starkman | 424/78 |
| 3,826,232 | 7/1974 | Duffey et al. | 119/157 |
| 3,896,807 | 7/1975 | Buchalter | 424/28 |
| 3,939,260 | 2/1976 | Lafon | 424/28 |
| 4,094,970 | 6/1978 | Behrenz et al. | 424/78 |
| 4,150,109 | 4/1979 | Dick et al. | 424/28 |
| 4,189,467 | 2/1980 | Von Bittera et al. | 424/28 |
| 4,225,578 | 9/1980 | Von Bittera et al. | 424/28 |
| 4,344,930 | 8/1982 | Maccrae et al. | 424/28 |

FOREIGN PATENT DOCUMENTS

| | | | |
|---|---|---|---|
| 0074626 | 3/1983 | European Pat. Off. | 424/365 |
| 2248813 | 4/1973 | Fed. Rep. of Germany | 424/28 |
| 52-28942 | 3/1977 | Japan | 424/32 |

OTHER PUBLICATIONS

Ahrens et al. (I), J. Econ. Entomol., 71(5): 764–765, Oct. 1978.
Ahrens et al. (II), J. Econ. Entomol., 70(3): 581–585, Oct. 1977.
Gladney, J. Econ. Entomol., 69(6): 757–760, Dec. 1976.
Quick, Vet. Med. Small Anim. Clin., 66: 773–774, Aug. 1971.
Harvey et al (I), J. Econ. Entomol., 63(5): 1688–1689, Oct. 1970.
Harvey et al. (II), J. Econ. Entomol., 61(4): 1128–1129, Aug. 1968.
Kirk et al., Current Veterinary Therapy Small Animal Practice (VI), published 1977, W. B. Saunders Co., Phila., Pa., pp. 109–115, 506–513, 547–554, 571–575.
Muller, J.A.V.M.A., 157(11): 1616–1626, Dec. 1, 1970, Flea Collar Dermatitis in Animals.
Breen et al., Vet. Med./Small Anim. Clin., 66: 1181–1183, Dec. 1971, Flea Collar Contact Dermatitis.
Bell et al., J.A.V.M.A., 167(7): 579–586, Oct. 1, 1975, Ataxia Depression and Dermatitis Associated with the Use of Dichlorvos-Impregnated Collars in Lab. Cat.
Fisch et al., J.A.V.M.A., 171(3): 269–270, Aug. 1, 1977, Evaluation of a Carbamate-Impregnated Flea and Tick Collar for Dogs.
Skawright et al., Australian Vet. Jl., 53: 509–514, Nov. 1977, Some Toxicity Aspects of Dichlorovos Flea Collars in Cats.
Allen at al., Feline Practice, 8(3): 9–16, May 1978, Evaluation of the Feline Dichlorovos (DDVP) Flea Collar.
Kieffer et al., British Medical Jl., I(6177): 1539–1540, Jun. 1979, Prurigo and Pets The Benefit from Vets.
Wilkins, Vet. Record, 107(13): 311, Sep. 27, 1980, Problems in Cats Caused by Flea Collars.

(List continued on next page.)

Primary Examiner—Shep K. Rose
Attorney, Agent, or Firm—Sprung Horn Kramer & Woods

[57] ABSTRACT

The invention relates to ectoparasiticide-containing polyurethane collars for animals containing spreading agents and ectoparasiticides as well as methods for their manufacture.

12 Claims, 1 Drawing Figure

OTHER PUBLICATIONS

Stillman et al., Contact Dermatitis, I: 65–69, (1975), Relative Irritancy of Free Fatty Acids of Different Chain Length.

Prottey et al., J. Invest. Dermatol., 64: 228–234, Apr. 1975, Correction of the Cutaneous Manifestations of Essential Fatty Acid Deficiency in Man by Application of Sunflower Seed Oil to the Skin.

Friedman et al., Pediatrics, 58(5): 650–654, Nov. 1976, Correction of Essential Fatty Acid Deficiency in Newborn Infants by Cutaneous Application of Sunflower Seed Oil.

Skolnik et al., Arch Dermatol, 113: 939–941, Jul. 1977, Human Essential Fatty Acid Deficiency-Treatment by Topical Application of Linoleic Acid.

Derwent Publications Ltd., Abstract No. 22083C/13, Insecticidal Ear Tags for Animals Esp. Cattle, Shel 9/20/78.

Derwent Publications Ltd., Abstract No. 12674Y/07, Control of Ear Ticks in Domestic Animals, Ciba 6/17/75.

Derwent Publications Ltd., Abstract No. 31552X/17, Hog Louse Control Ear Tag-With Barbed Spike, Meek 9/30/74.

Derwent Publications Ltd., Abstract No. 55661U-C, Tick Eradicator-With Plastic Strip, Ohl 8/21/72.

Derwent Publications Ltd., Abstract No. 22382X/12, Arthropod Repellent for Animal Ear-With Insecticide, Okla 2/24/75.

Derwent Publications Ltd., Abstract No. 66326B/37, Pesticidal Ear Tag for Animals, Shel 3/7/78.

Derwent Publications Ltd., Abstract No. 05077J/49, Pest Controlling Ingredient Reservoir, Icil 5/27/81.

Derwent Publications Ltd., Abstract No. 02739D/03, Insecticidal Collar for Animals, Ashe 6/14/79.

Derwent Publications Ltd., Abstract No. 15325D/09, Bio:Erodable Material Contg. A Drug, Alza 12/27/72.

Derwent Publications Ltd., Abstract No. 17132D/10, Synthetic Control of Parasitic Insects on Animals, Farn 7/16/79.

Derwent Publications Ltd., Abstract No. 51682D/29, Antiparasitic Animal Collar., Phar. 3/2/81.

Derwent Publications Ltd., Abstract No. 37573E/19, Polyurethane Ectoparasiticidal Collars for Pets, Farb 10/22/80.

Derwent Publications Ltd., Abstract No. 44165E/22, Pet Collar Contg. Recrystallised Phosmet., Zoec 11/14/80.

Derwent Publications Ltd., Abstract No. 38061T-AC, DDVP-Contg. Insecticidal Device-For Wearing by Domestic Animals, Dup. 4/1/71.

Derwent Publications Ltd., Abstract No. 40821S, Pesticidal Compsns. Contg. DDVP (used in the form of an animal collar), Shel 12/5/69.

Derwent Publications Ltd., Abstract No. 31242V/17, Heterocyclyl-(Thio)Phosphates-As Insecticides and Fungicides, Arie 7/19/72.

Derwent Publications Ltd., Abstract No. 11621C/07, Collar for Pets, Esp. Cats and Dogs, Eart 6/12/78.

Derwent Publications Ltd., Abstract No. 68521C/39, Pet Collar Impregnated with Insecticidal Pyrethroid, Nisq 2/7/79.

Derwent Publications Ltd., Abstract No. 38525A/22, Insecticidal Plastics Animal Collars, Robn 1/10/77.

Derwent Publications Ltd., Abstract No. 44356A/25, PVC Based Acaricide Compsns. Contg. Spiro-Cyclopropane, Amcy 12/13/76.

Derwent Publications Ltd., Abstract No. 29463W/18, Insecticidal Vaporising Strips-Contg. a Halophenyl, Arie 7/16/73.

Derwent Publications Ltd., Abstract No. 55045D/30, Water-Insol. Hydrophilic Gels Useful e.g. as Carriers for Drugs, Ciba 6/27/74.

ECTOPARASITICIDE-CONTAINING COLLARS FOR PETS

This is a continuation of application Ser. No. 308,718, filed 10/5/81, now abandoned. This application is also related to copending application Ser. No. 475,008, filed Mar. 14, 1983, which is a continuation of application Ser. No. 308,716, filed Oct. 5, 1981, now abandoned.

The present invention relates to ectoparasiticide-containing polyurethane collars which are used for animals, especially pets, and contain spreading agents and ectoparasiticides.

The commercially available PVC collars which have an ectoparasiticidal action and have hitherto been described, for small domestic animals, generally consists of thermoplastic polyvinyl chloride into which an ectoparasiticidal active compound, for example O,O-dimethyl dichlorovinyl phosphate, has been incorporated by co-extrusion. Such collars occasionally lead to damage to the skin of the animal; another disadvantage is the short effective life of the collar as a result of the relatively high vapour pressure of O,O-dimethyl dichlorovinyl phosphate ($1.2 \times 10^{-1}$ mm Hg).

Animal collars which are based on plasticised, thermoplastic polymers, preferably plasticised polyvinyl chloride, and which contain, as insecticidal active compounds, carbamates which have a lower volatility are described in U.S. Pat. No. 3,852,416. Whilst highly volatile active compounds, such as O,O-dimethyl dichlorovinyl phosphate rapidly pass directly into the gas phase from the ectoparasiticidally active plastic collars known hitherto, ectoparasiticides with a lower volatility, such as the carbamates mentioned, diffuse slowly out of the collar and form a white, dust-like layer on its surface. Some of the active compound passes into the vapour phase by sublimation and is effective in this phase, and another portion is distributed as a dust over the animal to be treated.

The said effluorescence or exudation of the active compound at the surface of the collar has a number of disadvantages.

If the collar is stored for a prolonged period before use, a relatively large amount of the active compound diffuses to the surface and becomes concentrated there. When the collar is used, there is then a very high dose of the ectoparasiticide on the surface, which indeed ensures a good immediate action but may already be at the limit of toxicity for the animal.

The active compound present on the surface is rapidly rubbed off. However, the active substance within the lower layers of the collar subsequently diffuses to the surface only very slowly. Release of the ectoparasiticide thus does not take place in the desired manner, that is to say uniformly over as long a period as possible.

The dust-like, whitish active compound present on the surface of the animal collar further imparts an extremely unattractive, dusty or mouldy appearance to the collar.

In the case of O,O-dimethyl dichlorovinyl phosphate and in the case of carbamates, the release of active compound is influenced by the plasticisers customary in PVC, such as phthalates and adipates.

The abovementioned difficulties can be avoided if polyurethanes which cannot be swollen in water and which contain certain amounts of spreading agents, such as spreading oils are used as carriers for the various active compounds or combinations thereof. Spreading oils are understood as those oily liquids which spread particularly well on the skin. They are known as such in the cosmetics industry. According to a proposal by R. Keymer, Pharm. Ind. 32, 577 (1970), they can be characterised, for example, by their surface tension towards air and this should be less than 30 dynes/cm. According to the present invention there are provided ectoparasiticide-containing polyurethane collars which are used for animals, especially pets, and which comprise a hydrophobic polyurethane which cannot be swollen in water (as hereinafter defined) and contains, relative to the polyurethane, 2 to 30% by weight, preferably 5 to 20% by weight, of an ectoparasiticide or a combination of ectoparasiticides and, relative to the polyurethane, 5 to 35% by weight, preferably 8 to 25% by weight, of a spreading agent.

By "hydrophobic" or "cannot be swollen" there are understood, according to the invention, polyurethanes which, when immersed in water at 20° C., absorb less than 2% by weight, preferably less than 0.5% by weight, of water in the course of 24 hours as a result of swelling.

As well as being produced by technically uncomplicated manufacturing process, the pet collars according to the invention have the advantage, above all, that the active compound is released continuously and in an essentially uniform manner over a period of some months.

In particular, surprisingly, the active compound diffuses out of the collar onto the surface in a graduated manner such that from there it is uniformly released into the environment by sublimation or by a mechanical route. No noticeable effluorescence forms on the surface, and when the collar is stored for a prolonged period, its pleasant appearance is preserved and no toxicity problems arise. The period of activity is significantly increased, and can be influenced by the controlled use of spreading agents.

The active compound is not deposited on the surface of the collar in the form of visible crystals, so that the collars according to the invention do not have a dusty appearance either on the surface or on the underside. Nevertheless, the collars are effective over a period of more than 4 months, as is illustrated in more detail in the following Examples. The in vitro release experiments show that the active compound is released continuously from the collars according to the invention even after prolonged storage, whilst most of the active compound has already diffused out of a comparable collar based on polyvinyl chloride after a short time. Thereafter, only a very small amount of the ectoparasiticide is released per unit time.

Possible ectoparasiticides are carbamates with a vapour pressure of between about $10^{-4}$ and $10^{-4}$ mm Hg at 20° C. Such compounds are mentioned, for example, in U.S. Pat. No. 3,852,416; their preparation is described in U.S. Pat. Nos. 2,903,478 and 3,203,853.

2-Isopropoxypheny N-methyl-carbamate with a vapour pressure of $6.5 \times 10^{-6}$ mm Hg is preferably employed in collars according to the invention as the ectoparasiticidal component.

Other carbamates which are suitable for use in collars according to the invention are, for example, 3-tolyl N-methylcarbamate, 3,4-xylyl-N-methylcarbamate, m-(1-methylbutyl)-phenyl N-methylcarbamate, 2-ethylthiomethyl-phenyl N-methylcarbamate, 4-dimethylamino-m-tolyl N-methylcarbamate, 2,3-dihydro-2,2-dimethylbenzofuran-7-yl N-methylcarbamate, 2-dimethylcarbamoyl-3-methyl-5-pyrazolyl-dimethylcarbamate and 2-dimethylamino-5,6-dimethylpyrimidin-4-yl N,N-dimethylcarbamate.

Further possible ectoparasiticides are, in particular, synthetic pyrethroids, for example those of U.S. patent application Ser. No. 916,163, filed on June 16, 1978 of which Ser. No. 195,026, filed Oct. 8, 1980 is a division, but preferably 3-phenoxy-4-fluoro-α-cyanobenzyl 2,2-dimethyl-3-[2-(4-chlorophenyl)-2-chlorovinyl]-cyclopropanecarboxylate and isomers thereof.

The ectoparasiticides can be used individually or in combinations. Thus preferred ectoparasiticides for use in collars according to the invention are an insecticidally active carbamate or synthetic pyrethroid or a mixture of such active compounds. The content of ectoparasiticides is 2 to 30% by weight, preferably 5 to 20% by weight, relative to the polyurethane.

The polyurethanes used, in collars according to the invention, as the carrier material are prepared in a manner which is in itself known, by reaction of polyisocyanates with relatively high-molecular compounds which contain at least two groups which are reactive towards isocyanates, and, if appropriate, with low-molecular chain-lengtheners and/or monofunctional chain-stoppers.

Possible starting components in the preparation of the polyurethanes are aliphatic, cycloaliphatic, araliphatic, aromatic and heterocyclic polyisocyanates, such as are described, for example, by W. Siefken in Liebig's Annalen der Chemie, 562, pages 75 to 136. Examples which may be mentioned are: ethylene diisocyanate, tetramethylene 1,4-diisocyanate, hexamethylene 1,6-diisocyanate, dodecane 1,12-diisocyanate, cyclobutane 1,3-diisocyanate, cyclohexane 1,3- and 1,4-diisocyanate and any desired mixtures of these compounds, 1-isocyanato-3,3,5-trimethyl-5-isocyanatomethyl-cyclohexane (see DE-AS (German Published Specification) No. 1,202,785 and U.S. Pat. No. 3,401,190), hexahydrotoluylene 2,4- and 2,6-diisocyanate and any desired mixtures of these compounds; hexahydrophenylene 1,3- and/or 1,4-diisocyanate, perhydrodiphenylmethane 2,4'- and/or 4,4'-diisocyanate, phenylene 1,3- and 1,4-diisocyanate, toluylene 2,4- and 2,6-diisocyanate and any desired mixtures of these compounds; diphenylmethane 2,4'- and/or 4,4'-diisocyanate, naphthylene 1,5-diisocyanate, triphenylmethane 4,4',4"-triisocyanate, polyphenyl-polymethylene polyisocyanates, such as are obtained by aniline/formaldehyde condensation and subsequent phosgenation and as are described, for example, in British patent specification Nos. 874,430 and 848,671; m- and p-isocyanatophenyl-sulphonyl isocyanates according to U.S. Pat. No. 3,454,606; perchlorinated aryl polyisocyanates, such as are described, for example, in U.S. Pat. No. 3,277,138; polyisocyanates containing carbodiimide groups, such as are described in U.S. Pat. No. 3,152,162 and in U.S. Pat. No. 3,152,162; diisocyanates such as are described in U.S. Pat. No. 3,492,330; polyisocyanates containing allophanate groups, such as are described, for example, in British Patent Specification No. 994,890, German Patent Specification No. 761,626 and Publishd Dutch Patent Application No. 7,102,524; polyisocyanates containing isocyanurate groups, such as are described, for example, in U.S. Pat. No. 3,001,973, in GB Patent Application No. 43 841, GB Patent Specification No. 1 091 949, in GB Patent Application No. 843 841, in GB Pat. No. 1 267 011 and in U.S. Pat. No. 3,879,316; polyisocyanates containing urethane groups, such as are described, for example, in German Patent Specification No. 752,261 or in U.S. Pat. No. 3,394,164; polyisocyanates containing acylated urea groups, according to U.S. Pat. No. 3,517,039; polyisocyanates containing biuret groups, such as are described, for example, in U.S. Pat. No. 3,124,605, in U.S. Pat. Nos. 3,124,605 and 3,201,372, and in British Patent Specification No. 889,050; polyisocyanates which have been prepared by telomerisation reactions and such as are described, for example, in U.S. Pat. No. 3,654,106; polyisocyanates containing ester groups, such as are mentioned, for example, in British Patent Specification Nos. 965,474 and 1,072,956, in U.S. Pat. No. 3,567,763 and in GB Patent Specification No. 1 086 404 reaction products of the abovementioned isocyanates with acetals, according to U.S. Pat. No. 3,120,502 and polyisocyanates containing polymeric fatty acid radicals, according to U.S. Pat. No. 3,455,883.

It is also possible to use the distillation residues which are obtained in the industrial preparation of isocyanates and contain isocyanate groups, these distillation residues being dissolved, if appropriate, in one or more of the abovementioned polyisocyanates. It is furthermore possible to use any desired mixtures of the abovementioned polyisocyanates.

Preferred polyisocyanates are in general the toluylene diisocyanates and the diphenylmethane diisocyanates.

Further starting components for the preparation of the polyurethanes are compounds which have at least two hydrogen atoms which are reactive towards isocyanates and have as a rule a molecular weight from 400 to 10,000. By these compounds there are understood, in addition to compounds containing amino groups, thiol groups or carboxyl groups, preferably polyhydroxy compounds, in particular compounds containing two to eight hydroxyl groups, and especially those with a molecular weight of 800 to 10,000, preferably 1,000 to 6,000, for example polyesters, polyethers, polythioethers, polyacetals, polycarbonates and polyester-amides containing at least two, as a rule 2 to 8 but preferably 2 to 4, hydroxyl groups, such as are in themselves known for the preparation of homogeneous and cellular polyurethanes.

The possible polyesters containing hydroxyl groups are, for example, reaction products of polyhydric, preferably dihydric and optionally additionally trihydric, alcohols and polybasic, preferably dibasic, carboxylic acids. Instead of the free polycarboxylic acids, it is also possible to use the corresponding polycarboxylic acid anhydrides or corresponding polycarboxylic acid esters of lower alcohols or mixtures thereof for the preparation of the polyesters. The polycarboxylic acids can be aliphatic, cycloaliphatic, aromatic and/or heterocyclic in nature and can optionally be substituted, for example by halogen atoms, and/or unsaturated.

Examples of these compounds which may be mentioned are: succinic acid, adipic acid, suberic acid, azelaic acid, sebacic acid, phthalic acid, isophthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimeric and trimeric fatty acids, such as oleic acid, optionally mixed with monomeric fatty acids, terephthalic acid dimethyl ester terephthalic acid bis-glycol ester.

Possible polyhydric alcohols are, for example, ethylene glycol, propylene 1,2- and 1,3-glycol, butylene 1,4- and 2,3-glycol, hexane-1,6-diol, octane-1,8-diol, neopentylglycol, cyclohexanedimethanol(1,4-bis-hydroxymethylcyclohexane), 2-methyl-propane-1,3-diol, glycerol, trimethylolpropane, hexane-1,2,6-triol, butane-1,2,4-triol, trimethylolethane, pentaerythritol, quinitol, mannitol and sorbitol, methyl glycoside, and furthermore diethylene glycol, triethylene glycol, tetraethylene glycol, polyethylene glycols, dipropylene glycol, polypropylene glycols, dibutylene glycol and polybutylene glycols. The polyesters can contain a proportion of terminal carboxyl groups. Polyesters from lactones, for example ε-caprolactone, or hydroxycarboxylic acids, for example ω-hydroxycaproic acid, can also be employed.

The polyethers which are possible according to the invention and which contain at least two, as a rule two to eight and preferably two or three, hydroxyl groups are also those of a type which is in itself known, and they are prepared, for example, by self-polymerisation of epoxides, such as ethylene oxide, propylene oxide, butylene oxide, tetrahydrofuran, styrene oxide or epichlorohydrin, for example in the presence of $BF_3$, or by addition of these epoxides, optionally as mixtures or successively, onto starting components with reactive hydrogen atoms, such as water, alcohols, ammonia or amines, for example ethylene glycol, propylene 1,3- or 1,2-glycol, trimethylolpropane, 4,4'-dihydroxy-diphenylpropane, aniline, ethanolamine or ethylenediamine. Sucrose polyethers such as are described, for example, in U.S. Pat. No. 3,222,357 and in U.S. patent application Ser. Nos. 153,002, 630,067 and 658,020, are also possible according to the invention. Those polyethers which predominantly (to the extent of up to 90% by weight, relative to all the OH groups present in the polyether) contain primary OH groups are frequently preferred. Polyethers which have been modified by vinyl polymers and such as are formed, for example, by polymerisation of styrene and acrylonitrile in the presence of polyethers (U.S. Pat. Nos. 3,383,351, 3,304,273, 3,523,093 and 3,110,695 and German Patent Specification No. 1,152,536) are also suitable, as are polybutadienes containing OH groups.

Polythioethers which may be mentioned are, in particular, the condensation products of thiodiglycol with itself and/or with other glycols, dicarboxylic acids, formaldehyde, aminocarboxylic acids or aminoalcohols. The products are mixed polythioethers, polythioether-esters or polythioether-ester-amides, depending on the co-components.

Possible polyacetals are, for example, the compounds which can be prepared from glycols, such as diethylene glycol, triethylene glycol, 4,4'-dihydroxyethoxydiphenyldimethylmethane or hexanediol, and formaldehyde. Polyacetals which are suitable according to the invention can also be prepared by polymerisation of cyclic acetals.

Possible polycarbonates containing hydroxyl groups are those of the type which is in itself known and which can be prepared, for example, by reacting diols, such as propane-1,3-diol, butane-1,4-diol and/or hexane-1,6-diol, diethylene glycol, triethylene glycol or tetraethylene glycol, with diaryl carbonates, for example diphenyl carbonate, or phosgene.

The polyester-amides and polyamides include, for example, the predominantly linear condensates obtained from polybasic saturated or unsaturated carboxylic acids or anhydrides thereof and polyhydric saturated or unsaturated aminoalcohols, diamines, polyamines or mixtures thereof.

Polyhydroxy compounds which already contain urethane or urea groups, and optionally modified naturally occurring polyols, such as castor oil, carbohydrates or starch, can also be used. It is also possible to employ, according to the invention, products obtained by adding alkylene oxides onto phenol/formaldehyde resins or onto urea/formaldehyde resins.

Representatives of these compounds to be used according to the invention are described, for example, in High Polymers, Volume XVI, "Polyurethanes, Chemistry and Technology", by Saunders-Frisch, Interscience Publishers, New York, London, Volume I, 1962, pages 32–42 and pages 44–54 and Volume II, 1964, pages 5–6 and 198–199, and in Kunststoff-Handbuch (Plastics Handbook), Volume VII, Vieweg-Höchtlen, Carl-Hanser-Varlag, Munich, 1966, for example on pages 45–71.

It is, of course, also possible to employ mixtures of the abovementioned compounds which have at least two hydrogen atoms which are reactive towards isocyanates and a molecular weight of 400–10,000, for example mixtures of polyethers and polyesters.

Further starting components which are to be employed, if appropriate, are compounds which have at least two hydrogen atoms which are reactive towards isocyanates and a molecular weight of 32–400. In this case also, by these compounds there are understood compounds which contain hydroxyl groups and/or amino groups and/or thiol groups and/or carboxyl groups, preferably compounds which contain hydroxyl groups and/or amino groups, and which serve as chain-lengtheners or crosslinking agents. These compounds as a rule have 2 to 8 hydrogen atoms which are reactive towards isocyanates, preferably 2 or 3 reactive hydrogen atoms.

Examples of such compounds which may be mentioned are: ethylene glycol, propylene 1,2- and 1,3-glycol, butylene 1,4- and 2,3-glycol, pentane-1,5-diol, hexane-1,6-diol, octane-1,8-diol, neopentylglycol, 1,4-bis-hydroxymethyl-cyclohexane, 2-methyl-propane-1,3-diol, glycerol, trimethylolpropane, hexane-1,2,6-triol, trimethylolethane, pentaerythritol, quinitol, mannitol and sorbitol, diethylene glycol, triethylene glycol, tetraethylene glycol, polyethylene glycols with a molecular weight of up to 400, dipropylene glycol, polypropylene glycols with a molecular weight of up to 400, dibutylene glycol, polybutylene glycols with a molecular weight of up to 400, 4,4'-dihydroxy-diphenylpropane, di-hydroxymethyl-hydroquinone, ethanolamine, diethanolamine, triethanolamine, 3-aminopropanol, ethylenediamine, 1,3-diaminopropane, 1-mercapto-3-aminopropane, 4-hydroxy or -amino-phthalic acid, succinic acid, adipic acid, hydrazine, N,N'-dimethylhydrazine, 4,4'-diaminodiphenylmethane, toluylenediamine, methylene-bis-chloroaniline, methylene-bis-anthranilic acid esters, diaminobenzoic acid esters and the isomeric chlorophenylenediamines.

In this case also, it is possible to use mixtures of different compounds which have at least two hydrogen atoms which are reactive towards isocyanates and a molecular weight of 32–400.

However, it is also possible to employ, according to the invention, polyhydroxy compounds containing high-molecular polyadducts or polycondensates in finely dispersed or dissolved form. Such modified polyhydroxy compounds are obtained when polyaddition reactions (for example reactions between polyisocyanates and compounds containing amino functional groups) or polycondensation reactions (for example between formaldehyde and phenols and/or amines) are allowed to proceed directly in situ in the abovementioned compounds containing hydroxyl groups. Such processes are described, for example, in U.S. Pat. Nos. 3,360,495, 3,325,421, 4,225,481, 4,042,537, 4,246,160, in U.S. patent application Ser. Nos. 578,050, 740,451 and in GB Patent Application No. 1 498 616.

However, it is also possible, according to U.S. Pat. No. 3,869,413 and DE-OS (German Published Specification) No. 2,550,860, to mix a finished aqueous polymer dispersion with a polyhydroxy compound and then to remove the water from the mixture.

When modified polyhydroxy compounds of the above-mentioned type are used as the starting component in the polyisocyanate polyaddition process, polyurethane plastics with substantially improved mechanical properties are formed in many cases.

When choosing the relatively high-molecular polyol component used for the preparation of the polyurethane, it must be taken into consideration that the finished polyurethane should not be swellable in water. The use of relatively large amounts of polyhydroxy compounds with ethylene oxide units (polyethylene glycol polyethers or polyesters with diethylene glycol or triethylene glycol as the diol component) should thus be avoided.

Hydrophobic polyesters, in particular those based on adipic acid and ethylene glycol and/or butanediol and/or neopentylglycol and/or hexanediol, polycarbonatediols and polyether-polyols based on propylene oxide or tetrahydrofuran are preferably employed. In order to render the polyurethane hydrophobic, it is also expedient in some cases (especially if relatively large amounts of mineral fillers are incorporated into the polyurethane) to co-use castor oil as the polyol component.

Catalysts are frequently also used in the preparation of the polyurethanes. Possible catalysts which are also to be used are those of the type which is in itself known, for example tertiary amines, such as triethylamine, tributylamine, N-methyl-morpholine, N-ethyl-morpholine, N-(coconut alkyl)-morpholine, N,N,N',N'-tetramethyl-ethylenediamine, 1,4-diaza-bicyclo-[2,2,2]octane, N-methyl-N'-dimethylaminoethyl-piperazine, N,N-dimethylbenzylamine, bis-(N,N-diethylaminoethyl)adipate, N,N-diethylbenzylamine, pentamethyldiethylenetriamine, N,N-dimethylcyclohexylamine, N,N,N',N-tetramethyl-1,3-butanediamine, N,N-dimethyl-$\beta$-phenylethylamine, 1,2-dimethylimidazole and 2-methylimidazole. Mannich bases, which are in themselves known, obtained from secondary amines, such as dimethylamine, and aldehydes, preferably formaldehyde, or ketones, such as acetone, methyl ethyl ketone or cyclohexane, and phenols, such as phenol, nonylphenol or bisphenol, can also be used as the catalysts.

Tertiary amines which contain hydrogen atoms which are active towards isocyanate groups and can be used as catalysts are, for example, triethanolamine, triisopropanolamine, N-methyl-diethanolamine, N-ethyl-diethanolamine and N,N-dimethylethanolamine, and reaction products thereof with alkylene oxides, such as propylene oxide and/or ethylene oxide.

Further possible catalysts are sila-amines with carbon-silicon bonds, such as are described, for example, U.S. Pat. No. 3,620,984, for example 2,2,4-trimethyl-2-silamorpholine and 1,3-diethylaminomethyltetramethyldisiloxane.

Nitrogen-containing bases, such as tetraalkylammonium hydroxides, as well as alkali metal hydroxides, such as sodium hydroxide, alkali metal phenolates, such as sodium phenolate, or alkali metal alcoholates, such as sodium methylate, are also possible catalysts. Hexahydrotriazines can also be employed as catalysts.

In addition, it is also possible to use organic metal compounds, in particular organic tin compounds, as catalysts.

Possible organic tin compounds are, preferably, tin-II salts of carboxylic acids, such as tin-II acetate, tin-II octanoate, tin-II ethylhexanoate and tin-II laurate, and tin-IV compounds, for example dibutyl-tin oxide, dibutyl-tin dichloride, dibutyl-tin diacetate, dibutyl-tin dilaurate, dibutyl-tin maleate or dioctyl-tin diacetate. All the abovementioned catalysts can, of course, be employed in the form of mixtures.

Further representatives of the catalysts to be used and details of the mode of action of the catalysts are given in Kunststoff-Handbuch (Plastics Handbook), Volume VII, published by Vieweg and Höchtlen, Carl-Hanser-Verlag, Munich 1966, for example on pages 96 to 102.

The catalysts are as a rule employed in an amount of between about 0.001 and 10% by weight, relative to the amount of compounds which have at least two hydrogen atoms which are reactive towards isocyanates and a molecular weight of 400 to 10,000.

Possible spreading agents (or "spreading oils") are the following substances: silicone oils of various viscosities; fatty acid esters, such as stearylic acid acetylester, lauric acid hexyl ester and dipropylene glycol pelargonate, esters of branched fatty acids of medium chain length with saturated $C_{16}$–$C_{18}$-fatty alcohols, for example isopropyl myristate and isopropyl palmitate, caprylic/capric acid esters of saturated fatty alcohols with a chain length of $C_{12}$–$C_{18}$, isopropyl stearate, oleic acid decyl ester and oleic acid oleyl ester, wax-like fatty acid esters, for example synthetic anatine uropygial gland fat, adipic acid diisopropyl ester and ester mixtures related to the latter, inter alia triglycerides, for example caprylic/capric acid triglyceride, triglyceride mixtures with vegetable fatty acids with a $C_8$–$C_{12}$ chain length or other specially selected naturally occurring fatty acids, mixtures of partial glycerides saturated or unsaturated with fatty acids which may also contain hydroxyl groups, and monoglycerides of $C_8$–$C_{10}$-fatty acids; fatty alcohols, such as isotridecyl alcohol, 2-octyldodecanol, cetylstearyl alcohol and oleyl alcohol; and fatty acids, such as oleic acid and stearic acid. Mixtures of one or more of these spreading agents may also be used.

Spreading agents which are particularly suitable are isopropyl myristate, isopropyl stearate, isopropyl palmitate, lauric acid hexyl ester, oleic acid decyl ester, dibutyl stearate, dibutyl sebacate, paraffin oil, ethylhexyl palmitage/stearate, isotridecyl stearate and a mixture of isopropyl myristate, isopropyl palmitate and isopropyl stearate.

The content of spreading agents is 5 to 35% by weight, preferably 8 to 25% by weight, relative to the polyurethane.

By fillers and additives which the collars according to the invention optionally contain there are to be understood the substances which are in themselves known in polyurethane chemistry, such as fillers and short fibres on an inorganic or organic basis, colouring agents, such as dyestuffs and coloured pigments, water-binding agents, surface-active solid substances or pH stabilisers.

Inorganic fillers which may be mentioned are, for example baryte, titanium dioxide, quartz sand, kaolin, carbon black and glass microbeads. Of the organic fillers for example, powders based on polystyrene or polyvinyl chloride can be employed.

Possible short fibers are, for example, glass fibres 0.1 to 1 mm in length of fibres of organic origin, such as, for example, polyesters or polyamide fibres. The dyestuffs or coloured pigments on an organic or inorganic basis which are in themselves known for colouring polyurethanes, such as iron oxide pigments or chromium oxide pigments and phthalocyanine pigments or monoazo pigments, can be used in order to impart the desired coloration to the collars according to the invention. Zeolites are the preferred water-binding agent. Solid surface-active substances which may be mentioned are, for example, cellulose powder, active charcoal, silica products and chrysotile asbestos.

It is possible to add pH-regulating substances, such as stearic acid or buffer systems based on inorganic phosphoric acid salts, to stabilise the ectoparasiticides against too rapid a decomposition.

The ectoparasiticide-containing collars according to the invention can be produced by the processes which are in themselves known in polyurethane chemistry, it being possible to obtain the collars according to the invention by thermoplastic processing methods or by reactive processes.

Thermoplastic polyurethanes such as are formed by reacting diisocyanates with higher-molecular dihydroxy compounds and low-molecular glycols as chain-lengtheners at a NCO/OH ratio of between about 0.97 and 1.05, are described, for example, in British patent specification Nos. 1,210,737, 1,270,836, 1,075,274, 1,110,118, 1,025,970, 1,057,018, 1,087,743 and 849,136, GB Patent Specification No. 1,346,012, GB Patent Appl. No. 781 469, U.S. Pat. No. 3,015,650, U.S. Pat. No. 2,871,218 and GB Patent Specification No. 1,438,145 and DE-OS (German Published Specification) No. 2,418,075.

The parasiticidal active compound can be added to these thermoplastic polyurethanes, which can be, for example, in granular form, together with the spreading agents in suitable mixing devices, for example in drums or in an extruder; however, it is also possible to add the active compound and spreading agent directly during the preparation of the polyurethane, if appropriate as a mixture with one of the starting components, for example in a process according to U.S. Pat. No. 3,963,679, the polyisocyanates and polyhydroxy compounds being reacted with one another continuously in a twin-screw extruder. In this process, however, care should be taken that the reaction temperature does not exceed the decomposition point of the active compound used as the ectoparasiticide.

Of the production methods which are in themselves known in polyurethane chemistry and are possible according to the invention and which are reactive mixtures, such as the casting process, spraying process or reactive injection-moulding process, the casting process is the procedure which is preferred according to the invention. In this procedure, the ectoparasiticide-containing collars can be produced in a manner which is in itself known, either by the one-stage process or by the prepolymer or semi-prepolymer process.

Of the process variants of the casting process, the one-stage process is particularly preferred according to the invention. In this case, the higher-molecular polyols, ectoparasiticidal active compound, spreading agent and, if appropriate, crosslinking agent and fillers and additives, and, finally, the catalyst are mixed together, and the isocyanate component is then mixed in.

The collars according to the invention can be produced continuously or discontinuously by the casting process. In the continuous procedure, the ectoparasiticide-containing reaction mixture is poured, and if necessary spread with a doctor blade, onto a conveyor belt. A continuous web is obtained, which can then be divided into individual strips corresponding to the dimensions of the desired collars. If it is intended to produce the collars discontinuously, the reaction mixture is poured into open or closed moulds of suitable dimensions and left to harden.

The conditions during the reaction can also be varied in a manner such that either compact or foamed polyurethanes are obtained. For example, if air is whipped into the reactive mixture, foams are obtained.

In the procedures of the casting process, the conveying, metering and mixing of the individual components or component mixtures can be effected using the devices which are in themselves known to the expert.

In the production of collars according to the invention, the ectoparasiticidal active compounds can also be added to solvent-free reactive systems which contain spreading agents and consist of a higher-molecular polyisocyanate component and a polyamine component and are described, for example, in GB Patent Specification No. 1,523,148.

It is, of course, also possible, in the production of collars according to the invention, to introduce the active compound into a solution of a polyurethane or polyurethane-urea and then to evaporate off the solvent. In this case also, higher temperatures must be avoided, so that no decomposition of the active compound occurs. It is therefore expedient to use solutions of polyisocyanate polyaddition products in weakly polar, highly volatile solvents or solvent mixtures. Such so-called "soft solvent" systems are described, for example, in U.S. Pat. No. 2,957,852, British Patent Specification No. 1,040,055, German Patent Specification No. 643,811, U.S. Pat. Nos. 3,609,112, 3,752,786 and 3,936,409 and U.S. Pat. Nos. 3,734,894, 3,912,680, 3,867,350 and 3,857,809.

Polar solvent systems (for example containing dimethylformamide or N-methylpyrrolidone) can also be used if the devolatilisation temperature is kept sufficiently low.

According to the invention, it is possible to form collars of polyurethane, without the use of a carrier, for example by injection-moulding one of the thermoplastics mentioned, or by the casting process, by allowing a reactive two-component system to react in a suitable mould. In many cases, however, it is desirable to impregnate and/or coat a suitable carrier material with one of the thermoplastic polyurethanes, reactive systems or one-component polyurethanes, dissolved in solvents which can easily be evaporated off, which are mentioned above and contain the active compound.

The present invention thus provides a process for the production of an animal collar according to the present invention comprising forming the collar of the hydrophobic polyurethane, without the use of a carrier, or impregnating and/or coating the hydrophobic polyurethane onto a collar of carrier material.

Possible carrier materials are the most diverse materials based on naturally occurring and/or synthetic raw materials, such as fleeces, knitted fabrics, mesh fabrics, woven fabrics, mats, foamed or compact plastic films, natural leather or imitation leather. In general, this carrier material is worn on the outer surface of the animal collar, and the coating with the ectoparasiticide-containing polyurethane is on the inner surface. In this manner, it is possible to give the animal collar virtually any desired appearance.

The animal collars according to the invention are used for animal, especially pets, in particular for dogs and cats. The collars according to the invention can be successfully used against numerous harmful animal ectoparasites from the class of Arachnida and the class of insects which live as parasites on dogs and cats.

The following Examples illustrate the present invention. Unless indicated otherwise, the parts given in the examples are parts by weight.

The following ectoparasiticidal active compounds are employed in the examples below:

"Active compound 1"=2-isopropoxyphenyl N-methyl-carbamate (propoxur)

"Active compound 2"=3-phenoxy-4-fluoro-α-cyano-benzyl 2,2-dimethyl-3-[2-(4-chlorophenyl)-2-chlorovinyl]-cyclopropanecarboxylate.

EXAMPLE 1

A collar was formed of the immediately following components A and B;

| Component A: | | |
| --- | --- | --- |
| Trihydroxy-polyether (m.w. 4,800) | 39.78 | parts |
| Butane-1,4-diol (crosslinking agent) | 5.00 | part |
| Pigment (iron oxide) | 0.50 | part |
| Active compound 1 | 11.40 | parts |
| Lauric acid hexyl ester | 18.00 | parts |
| Dibutyl-tin dilaurate | 0.03 | part |
| Component B: | | |
| 4,4'-Diisocyanatodiphenyl-methane, modified with tripropylene glycol, isocyanate content: 23% by weight | 24.80 | parts |

EXAMPLE 2

A collar was formed of the immediately following components A and B;

| Component A: | | |
| --- | --- | --- |
| Trihydroxy-polyether (m.w. 4,800) | 37.98 | parts |
| Butane-1,4-diol (crosslinking agent) | 5.00 | parts |
| Pigment (iron oxide) | 0.50 | part |
| Zeolite paste (1:1 in castor oil) | 0.50 | part |
| Active compound 1 | 11.40 | parts |
| Isopropyl myristate | 20.00 | parts |
| Dibutyl-tin dilaurate | 0.02 | part |
| Component B: | | |
| 4,4'-Diisocyanatodiphenyl-methane, modified with tripropylene glycol, isocyanate content: 23% by weight | 24.60 | parts |

EXAMPLE 3

A collar was formed of the immediately following components A and B;

| Component A: | | |
| --- | --- | --- |
| Trihydroxy-polyether (m.w. 4,800) | 31.063 | parts |
| Butane-1,4-diol | 5.000 | parts |
| Pigment (iron oxide) | 0.500 | parts |
| Zeolite paste (1:1 in castor oil) | 0.500 | part |
| Active compound 1 | 11.400 | parts |
| Active compound 2 | 7.600 | parts |
| Isopropyl myristate | 20.000 | parts |
| Dibutyl-tin dilaurate | 0.037 | part |
| Component B: | | |
| 4,4'-Diisocyanatodiphenyl-methane, modified with tripropylene glycol, isocyanate content: 23% by weight | 23.90 | parts |

EXAMPLE 4

A collar was formed of the immediately following components A and B;

| Component A: | | |
| --- | --- | --- |
| Trihydroxy-polyether (m.w. 4,800) | 36.273 | parts |
| Butane-1,4-diol | 5.000 | parts |
| Pigment (iron oxide) | 0.500 | parts |
| Zeolite paste (1:1 in castor oil) | 0.500 | part |
| Active compound 1 | 11.400 | parts |
| Active compound 2 | 3.800 | parts |
| oleic acid decyl ester | 18.000 | parts |
| Dibutyl-tin dilaurate | 0.027 | part |
| Component B: | | |
| 4,4'-Diisocyanatodiphenyl-methane, modified with tripropylene glycol, osocyanate content: 23% by weight | 24.500 | parts |

EXAMPLE 5

A collar was formed of the immediately following components A and B;

| Component A: | | |
| --- | --- | --- |
| Trihydroxy-polyether (m.w. 4,800) | 45.5 | parts |
| Butane-1,4-diol | 5.0 | part |
| Active compound 1 | 15.0 | parts |
| Pigment (iron oxide) | 0.5 | part |
| Zeolite paste (1:1 in castor oil) | 0.5 | part |
| Ester of a branched fatty acid with saturated $C_{12}$–$C_{18}$-fatty alcohols | 8.0 | parts |
| Dibutyl-tin dilaurate | 0.02 | part |
| Component B: | | |
| 4,4'Diisocyanatodiphenyl-methane, modified with tripropylene glycol, isocyanate content: 23% by weight | 25.5 | parts |

The collars according to Examples 1 to 5 were produced continuously by the casting process with the aid of a belt installation. The polyether, active compound or active compound combination, colour paste, zeolite paste, spreading agent and butane-1,4-diol were mixed together in a kettle which could be heated and the mixture was warmed to 60° C. The catalyst (dibutyl-tin dilaurate) was then admixed.

The resulting mixture was the component A, which was mixed with the respective component B by means of a mixing unit. The mixing head was attached to a sideways traversing device which moves to and fro. The reaction mixture flowed continuously out of the mixing head onto imitation leather (for example as a coating thereon) or onto a web of plastic. The reaction mixture started to react 30 seconds after leaving the mixing head and had hardened after about 60 seconds.

The temperature in the polyurethane material rose to about 90° C. within 2 minutes and remained at 90° C. for a period of 1 minute.

The web then passed through a cooling zone. The product had solidified to such an extent that it could be passed over a system of slowly revolving V-belts to the cutting device.

Polyurethane compositions were cast, by the prepolymer process (via isocyanate prepolymers), from each of the combinations of polyurethane components, spreading agents and active compounds listed in the following Examples 6 to 8 and were then granulated. The granules were converted to collars by the injection-moulding process.

EXAMPLE 6

40.4 parts of a polyester obtained from butane-1,4-diol and adipic acid (m.w. 2,000)
5.14 parts of 1,4-butanediol and diphenylmethane 4,4'-diisocyanate in an amount corresponding to a NCO-/OH ratio of 1.03,
15 parts of active compound 1 and
18 parts of isopropyl myristate.

EXAMPLE 7

43.5 parts of a polyester obtained from ethylene glycol, butanediol and adipic acid (m.w. 2,000),
5.65 parts of butane-1,4-diol and diphenylmethane 4,4'-diisocyanate in an amount corresponding to a NCO-/OH ratio of 1.03,
10 parts of active compound 1,
2.5 parts of active compound 2 and
15 parts of lauric acid hexyl ester.

EXAMPLE 8

25 parts of a polypropylene glycol ether (m.w. 2,000)
25 parts of a polyester obtained from butane-1,4-diol and adipic acid (m.w. 2,000)
4.5 parts of butane-1,4-diol and diphenylmethane 4,4'-diisocyanate in an amount corresponding to a NCO-/OH ratio of 1.03,
10 parts of active compound 1,
5 parts of active compound 2 and
16 parts of isopropyl myristate.

EXAMPLE 9

20 g of active compound 1 were dissolved in 50 g of methyl ethyl ketone at room temperature, with occasional stirring. 25 g of N-methylpyrrolidone and 15 parts of isopropyl myristate were then added and 25 g of a granular thermoplastic polyurethane were dissolved in the mixture thus obtained.

The solution was cast to a film 1 mm thick and the solvents were removed in a drying cabinet at 100° to 150° C. in the course of 60 minutes. A homogeneous, transparent film from which the active compound did not effluoresce even on prolonged storage was formed.

The polyurethane was prepared by reacting 100 parts of a polyester of butanediol, ethylene glycol and adipic acid (OH number: 51.7), 7.5 parts of butane-1,4-diol and 31.3 parts of 4,4'-diisocyanatodiphenylmethane (NCO-/OH=0.97) in a reaction screw in accordance with the method of DE-OS (German Published Specification) No. 2,302,564.

COMPARISON EXPERIMENT 1

The in vitro release (release of active compound) of active compound 1 from the polyurethane system according to the invention prepared as in Examples 1 and 2 was compared with the result obtained with a conventional PVC collar containing propoxur (see FIG. 1).

The in vitro release of the active compound 1 was determined over a period of weeks by standardised and gentle rubbing with fur rollers, which permitted differentiated evaluation of various systems.

These tests imitated mechanical rubbing off of the active compound on the animal.

In FIG. 1, the release of active compound in mg was plotted as the ordinate against the time in days as the abscissa. Curves A, B, C, D and E were as follows:
A denotes a PVC collar, stored at room temperature for 6 months and sealed in foil,
B denotes a PVC collar,
C denotes a PUR collar according to Example 1
D denotes a PUR collar according to Example 2
E denotes a PUR collar without a spreading agent

COMPARISON EXPERIMENT 2

The following long-term test was carried out with a dog collar according to the invention. It was compared with conventional PVC collars. In the following Table the row headed "Weeks" refers to stages in the duration of the test and the figures refer to the number of test animals killed, expressed as a percentage.

| Weeks | 1 | 8–9 | 12–13 | 15 |
|---|---|---|---|---|
| Test: fleas | | | | |
| PVC collar | 100 | 98 | 96 | 87 |
| PUR collar with a spreading agent and active compounds ½ in the ratio 10%/2.5% | 100 | 99 | 98 | 95 |
| Test: ticks | | | | |
| PVC collar | 100 | 67 | 43 | 29 |
| PUR collar with a spreading agent and active compounds ½ in the ratio 10%/2.5% | 100 | 90 | 78 | 72 |

What is claimed is:

1. An ectoparasiticide-containing polyurethane collar for animals, which comprises a hydrophobic polyurethane which cannot be swollen in water and which contains, relative to the polyurethane, 2 to 30% by weight of an ectoparasiticide, said ectoparasiticide selected from the group consisting of an insecticidally active carbamate having a vapor pressure of between about $10^{-4}$ and $10^{-6}$ mm Hg measured at 20° C., and an insecticidally active synthetic pyrethroid, and combinations thereof and, relative to the polyurethane, 8 to 25% by weight of a spreading agent, said speading agent selected from the group consisting of silicone oils, fatty acid esters, fatty alcohols, fatty acids and combinations thereof.

2. A collar according to claim 1, containing, relative to the polyurethane, 5 to 20% by weight of the ectoparasiticide or of a combination of ectoparasiticides.

3. A collar according to claim 1 characterised in that the polyurethane is a polyurethane which when kept in water at 20° C. for 24 hours, absorbs less than 0.5% by weight of water as a result of swelling.

4. An ectoparasiticide-containing polyurethane collar of claim 1, wherein the ectoparasiticide is 2-isopropoxyphenyl N-methylcarbamate.

5. An ectoparasiticide-containing polyurethane collar of claim 1, wherein the ectoparasiticide is 3-phenoxy-4- fluoro-α-cyano-benzyl-2,2-dimethyl-3-[2-(4-chlorophenyl)-2-chlorovinyl]-cyclopropanecarboxylate.

6. An ectoparasiticide-containing polyurethane collar of claim 1, wherein the combination of ectoparasiticides is a combination of 2-isopropoxyphenyl N-methylcarbamate and 3-phenoxy-4-fluoro-α-cyano-benzyl-2,2-dimethyl-3-[2-(4-chlorophenyl)-2-chlorovinyl]-cyclopropoanecarboxylate.

7. A process for the production of an animal collar according to claim 1, comprising forming the collar of the hydrophobic polyurethane, without the use of a carrier, or impregnating and/or coating the hydrophobic polyurethane onto a collar of carrier material.

8. A process according to claim 7, characterised in that the polyurethane is formed by casting.

9. A method for combating ectoparasities in animals which comprises applying to said animals an ectoparasiticide-containing collar of claim 1.

10. A collar according to claim 1, wherein said spreading agent is a fatty acid ester selected from the group consisting of stearylic acid acetyl ester, lauric acid hexyl ester, dipropylene glycol pelargonate, isopropyl myristate, isopropyl palmitate, caprylic/capric acid esters of saturated fatty alcohols with a chain length of $C_{12}$–$C_{18}$, isopropyl stearate, oleic acid decyl ester, oleic acid oleyl ester, synthetic anatineuropygial gland fat, adipic acid diisopropyl ester, caprylic/capric acid triglyceride, triglyceride mixtures with vegetable fatty acids with a $C_8$–$C_{12}$ chain length and mixtures of partial glycerides saturated or unsaturated with fatty acids.

11. A collar according to claim 1, wherein said spreading agent is a fatty alcohol selected from the group consisting of isotridecyl alcohol, 2-octyldodecanol, cetyl stearyl alcohol and oleyl alcohol.

12. A collar according to claim 1, wherein said spreading agent is a fatty acid selected from the group consisting of oleic acid and stearic acid.

* * * * *